United States Patent [19]
Schuerch et al.

[11] Patent Number: 5,564,765
[45] Date of Patent: Oct. 15, 1996

[54] MODULE SUSPENSION APPARATUS

[75] Inventors: Peter Schuerch, Mechanicsville; Arthur J. Shapiro, Maidens; Louis H. Piper, Richmond, all of Va.

[73] Assignee: Infilco Degremont, Inc., Richmond, Va.

[21] Appl. No.: 338,697

[22] Filed: Nov. 14, 1994

[51] Int. Cl.⁶ .............................. B66C 1/22; C02F 1/32
[52] U.S. Cl. .................. 294/81.56; 210/198.1; 210/748
[58] Field of Search ................. 294/81.1, 81.5, 294/81.51, 81.56, 81.61, 68.1, 68.3, 82.33, 110.1; 210/192, 198.1, 748; 422/186.3

[56] References Cited

U.S. PATENT DOCUMENTS

| | | | |
|---|---|---|---|
| 2,441,026 | 5/1948 | Long | 294/110.1 |
| 2,445,106 | 7/1948 | Dempster | 294/110.1 |
| 3,106,421 | 10/1963 | Wyrough | 294/81.51 |
| 3,148,909 | 9/1964 | Tantlinger | 294/81.5 |
| 3,285,650 | 11/1966 | Dukes | 294/110.1 |
| 4,671,724 | 6/1987 | Bolton | 294/81.51 |
| 5,368,826 | 11/1994 | Weltz et al. | 210/748 |

*Primary Examiner*—Dean Kramer
*Attorney, Agent, or Firm*—Miller & Christenbury

[57] ABSTRACT

Apparatus for positioning a module containing at least one ultraviolet lamp relative to a passageway in which fluid to be treated flows including a base member fixed to stable structure associated with the passageway and a suspender connected to the base member. The suspender includes a rotatably-mounted latch having a module-engaging portion sized and shaped to engage a module latch receiver associated with the module, a spring associated with the latch and adapted to urge rotation of the module-engaging portion toward and into engagement with the module latch receiver and a rotatably-mounted latch cover positioned adjacent the latch.

19 Claims, 8 Drawing Sheets

MODULE SUSPENSION APPARATUS

FIELD OF THE INVENTION

This invention relates to an apparatus for positioning modules, particularly to an apparatus for suspending ultraviolet disinfection modules in desired positions within a passageway in which liquids flow.

Background of the Invention

The need to disinfect municipal and industrial waste water has gained increasing importance in view of increased environmental awareness and regulations mandating improved water quality. Such water has been disinfected with ultraviolet radiation in a number of methods and with a variety of apparatus. Such methodologies and apparatus typically include surrounding ultraviolet sources with protective jackets (hereinafter sometimes referred to as "lamps") and submerging the lamps into the water as it flows through open or closed channels, open or closed containers or the like. One frequently used disinfection apparatus consists of a multiplicity of vertically oriented lamps contained within a module. The module is oftentimes constructed with an upper header located above the water and containing electronic components and a lower header located in the water stream and connected to the upper header with four vertically oriented legs.

The modules often contain sophisticated electronic monitoring and control equipment, including photocell detectors, ballasts, electronic lamp controllers, temperature controllers, temperature monitors, warning devices and the like. All of this equipment is subject to malfunction. Ease of access to the modules for analysis and repair is, therefore, highly advantageous. Also, it is advantageous to periodically inspect and maintain modules of the type described above on a weekly, monthly or yearly cyclical basis, for example.

In many cases, the modules are normally positioned in an inconvenient or difficult position regarding ease of access due to the uppermost portion of the modules being at or below ground level in a wastewater channel. As a result of the need for access, modules can be removed entirely from the channel or raised either partially or completely above, but not away from, the channel. To date this has been a difficult task at best or not possible due to the lack of suitable suspension apparatus capable of achieving this task. For example, one way to suspend a module partially out of the channel would be the use of standard crane module removal apparatus. However, the module is not secured in a fixed position but is free to swing about the crane wire. Use of the crane for suspending the module above the channel prevents it from other use with other modules. Thus, this method has proved unsatisfactory. Other apparatus dedicated solely to suspending the modules has proven to be bulky and limited in application and not capable of suspending multiple modules simultaneously at a desired height.

It is especially advantageous to be able to suspend the modules partially or completely above the channel in order to access the electronic equipment in the module upper header and/or to access lamp jackets for cleaning or maintenance or for lamp replacement. In accomplishing these tasks, it is highly advantageous to have the module secured in a fixed position, free of movement, since components of the modules are delicate and subject to damage. Accordingly, it is highly desirable to have a highly stable positioning of the module when suspended. Prior methodology and apparatus, such as the crane removal systems, has proven to be ineffective in this regard.

There are circumstances under which it is highly desirable to remove one or more of the modules from the water and the channel to better clean the lamps or other components of the module. There are a number of other reasons for removing one or more of the modules from the water over the course of time. For example, the modules typically contain a large number of lamps, such as 40 lamps or 48 lamps or more. These lamps have a limited life span and periodically must be replaced. Many modules are constructed to permit replacement of individual lamps while remaining in the water. However, placement of lamps in certain module constructions must occur after the module has been removed from the water to be treated. In other cases, it is simply more convenient to do so for reasons of water channel construction, channel width, treatment conditions and the like.

The need to remove modules from the water stream, sometimes multiple modules at the same time or to move them to a different location has resulted in the need for a means for effecting such removal and replacement that works in conjunction with a suspension apparatus. It is important that any means for suspending the modules works easily and in conjunction with the means for removing and replacing modules when they are periodically moved to a remote location from the channel. Thus, it is highly desirable to have a suspension apparatus that does not impede the removal and replacement of modules into the channel during periodic cleaning, monitoring, maintenance and repair.

Objects of the Invention

It is an object of the present invention to provide an apparatus capable of suspending modules at locations partially and/or completely out of the stream of water to be disinfected.

It is another object of the invention to provide an apparatus capable of suspending ultraviolet disinfection modules within or above a stream of water to be disinfected which does not impede the methods and apparatus used in placement of and removal from the water to be disinfected.

It is an important object of the invention to provide an apparatus capable of suspending ultraviolet disinfection modules or at least their electronic components above potential flood levels.

It is yet another object of the invention to provide an apparatus capable of suspending ultraviolet disinfection modules partially and/or completely out of the stream of water to be disinfected in fixed and stable conditions to facilitate monitoring, cleaning, maintenance and periodic repair.

Other objects and advantages of the invention will become apparent to those skilled in the art from the drawings, the detailed description of detailed embodiments, and the appended claims.

Summary of the Invention

The invention provides an apparatus for positioning a module containing at least one ultraviolet lamp in a passageway in which fluid to be treated flows. The apparatus includes a base member affixed to a wall of the passageway. At least one suspender connects to said base member. The suspender includes a rotatably mounted latch having a module engaging portion sized and shaped to engage a module latch receiver associated with the module. A spring connected to the latch urges rotation of the module engaging portion toward the module latch receiver. A rotatably mounted latch cover is positioned adjacent said latch and another spring connected to the latch cover urges rotation of the latch cover in a direction opposite the direction of rotation urged by the latch spring.

DETAILED DESCRIPTION OF THE INVENTION

It will be appreciated that the following description is intended to refer to the specific embodiments of the invention selected for illustration in the drawings and is not intended to define or to limit the invention, other than in the appended claims.

Figure 1:
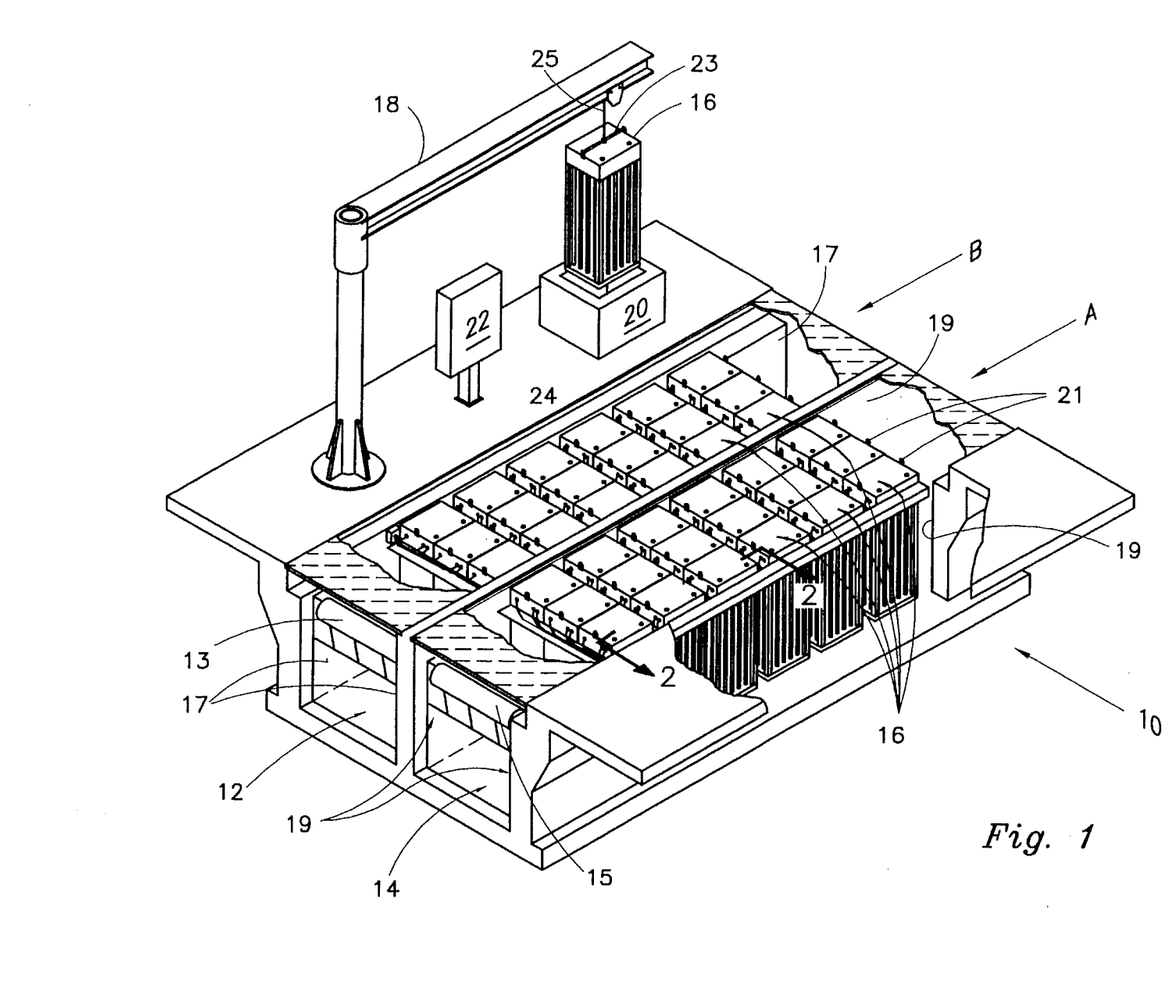
FIG. 1 is a schematic view of a multiplicity of ultraviolet disinfection modules located within parallel waste water channels, an accompanying control panel and module removal and cleaning apparatus.

Turning now to the drawings in general and FIG. 1 in particular, the number 10 designates a waste water disinfection system. System 10 in the embodiment shown includes two waste water channels 12 and 14, which are open channels having side walls 17 and 19 and a floor (not numbered). The level of waste water through channels 12 and 14 is controlled by gates 13 and 15, respectively, and preferably other gates not shown. A multiplicity of modules 16 are positioned in channels 12 and 14 in a series of six rows, each row having three modules aligned side by side. Modules 16 are portable and may be removed by crane 18, for example, and placed into a remotely located cleaning basin 20. Lifting rod 23 connects to lifting eyes 21 of modules 16. Lifting wire 25 connects between crane 18 and lifting rod 23 and is extendable and retractable to move modules 16 into desired positions in and out of channels 12 and 14. Control panel 22 assists in operation of the overall disinfection system 10 and connects directly to modules 16 via connections (not shown) and to a remote control location (not shown) via other connectors. Waste water to be disinfected flows through channels 12 and 14 in the direction shown by arrows "A" and "B", although flow in either direction is possible.

Figure 2:
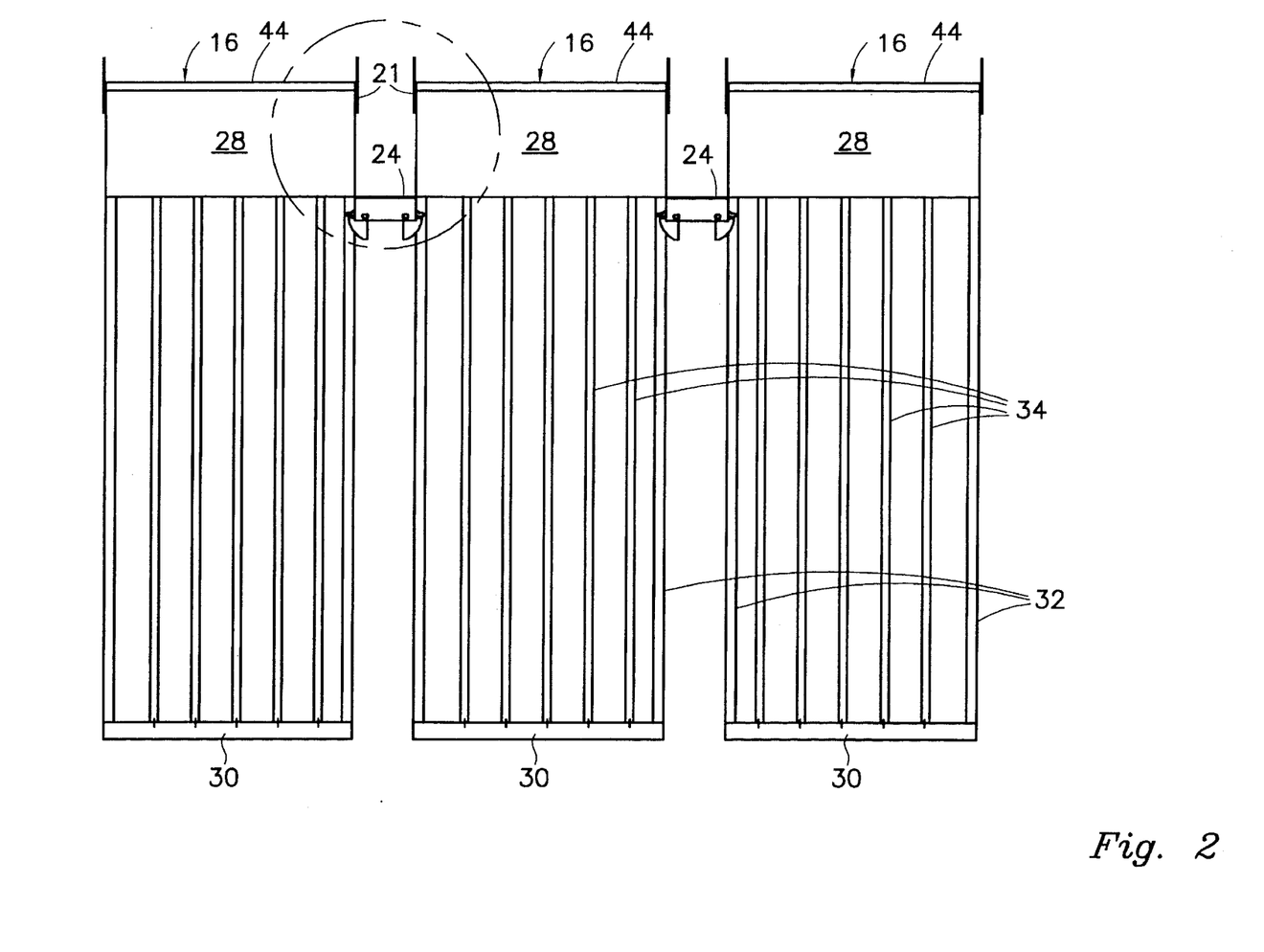
FIG. 2 is a schematic front elevational view of three of the modules shown in FIG. 1 taken along the lines and arrows 2—2 in FIG. 1.
Figure 3:
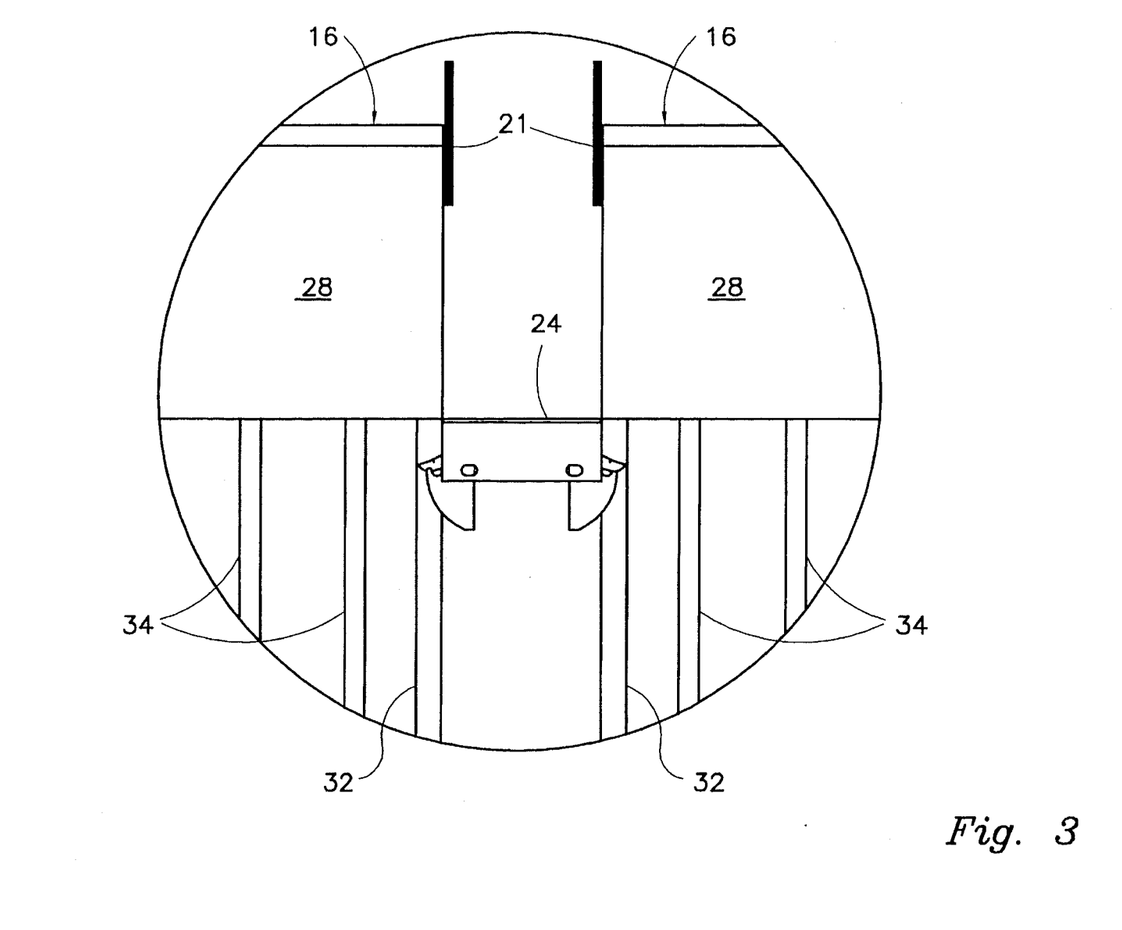
FIG. 3 is an exploded view of suspension apparatus associated with two modules shown in FIG. 2 from the area of the exploded line of FIG. 2.

Referring to FIGS. 2–3, modules 16 are shown in an enlarged form for ease of understanding. Modules 16, which are positioned in channels 12 and 14 as shown in FIG. 1, include a housing 28, a lower header 30 and support legs 32. A multiplicity of ultraviolet lamps 34 connect between housing 28 and lower header 30. Housing 28 has a power connection fitting, a data connection fitting, an air source connection fitting (all not shown) and other appropriate connections known in the art and not further discussed. Housing 28 is enclosed on all sides and has a hinged cover 44, which may be opened and closed, and locked in place with locks (not shown). Suspenders 24 are positioned between modules 16 and are described in detail below.

Figure 6:
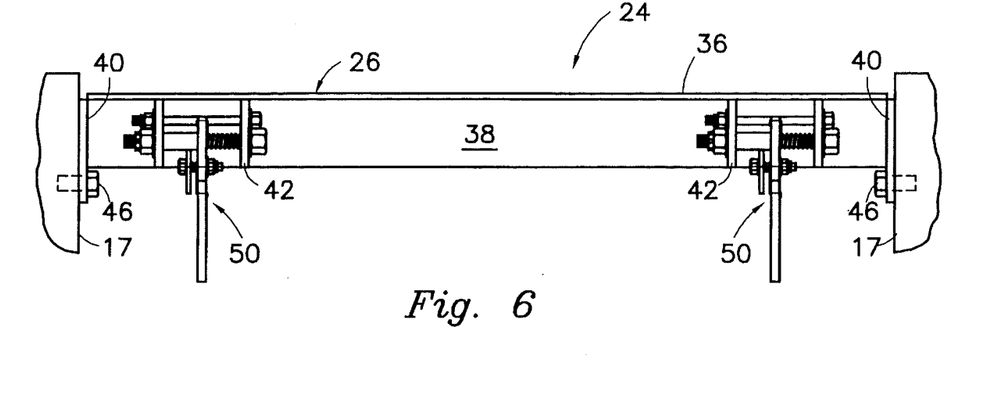
FIG. 6 is a front elevational view of the apparatus shown in FIGS. 4 and 5, and including a locking mechanism to form suspension apparatus mounted between channel walls.
Figure 7:
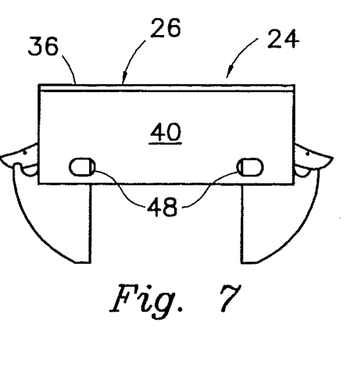
FIG. 7 is a side view of the apparatus shown in FIG. 6.

The specific construction of suspenders 24 is shown in FIGS. 4–7 which are referred to collectively below. Suspender 24 includes a base member 26. Base member 26 includes base plate 36, a pair of uprights 38 connected to and running longitudinally along base plate 36, a pair of end plates 40 connected to base plate 36 and uprights 38, and hanger plates 42 connected to base plate 36 and respective uprights 38. Each hanger plate 42 has a pair of hanger plate holes 57 and 78. In each pair of hanger plates 42, one plate has a spring receiving hole 51. Base member 26 is mounted to or affixed to side wall 17 with mounting screws 46 which extend through mounting holes 48 in end plates 40. The particular construction of locking mechanism 50, mounted between hanger plates 42 and as shown in FIG. 6, is described in detail with respect to FIGS. 8–12.

Referring now to FIGS. 8–12, locking mechanism 50 includes latch 52 in an "at rest" position and mounted on latch screw 54 which extends through hanger plate holes 57 and between washers 56 and hanger plates 42. Latch 52 has surface edges including curved surface 59, locking tip 61, locking groove 65 and locking wall 63. Latch 52 also has latch hole 53, latch cover screw hole 68 and spring holes 62 and 74. Latch hole cylinder extends substantially perpendicularly outwardly from latch 52.

Locking mechanism 50 also includes latch cover 64 mounted onto latch 52. Latch screw 54 extends through latch hole 53 and latch hole cylinder 55. Latch hole cylinder 55, in conjunction with torsion spring 60, maintains latch 52 in a desired position spaced between hanger plates 42. Latch screw 54 is secured between hanger plates 42 with washers 56 mounted exteriorly of hanger plates 42 and by lock nut 58. Torsion spring 60 is also mounted on latch screw 54 and is anchored on one end on hanger plate 42 and on the opposite end through spring hole 62 on latch 52.

Latch cover 64 is mounted to latch 52 by latch cover screw 66 which extends through latch cover screw hole 68 of latch 52 and is secured in place by washers 56 and lock nut 58. Torsion spring 70 is mounted around latch cover screw 66 and extends between spring hole 72 of latch cover 64 and spring hole 74 of latch 52. Stop screw 76 also extends between hanger plates 42 by way of hanger plate holes 78 and is held into a desired position with washers 56 and lock nut 58.

Figure 8:
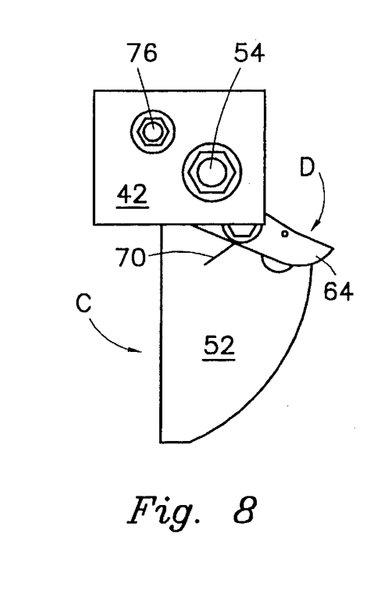
FIG. 8 is an enlarged front elevational view of latch apparatus partially shown in FIG. 7.
Figure 9:
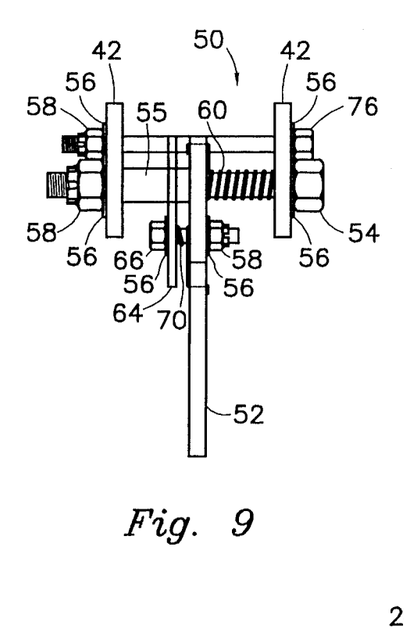
FIG. 9 is an enlarged side view of the latch apparatus portion of the suspension apparatus shown in FIG. 6.
Figure 10:
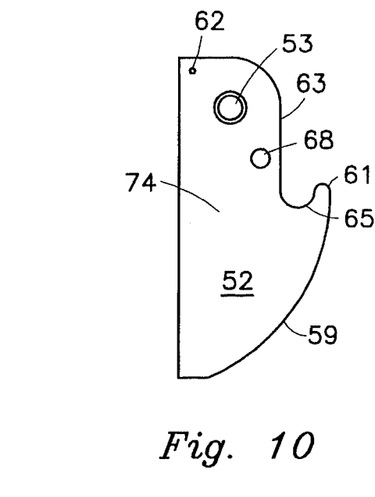
FIG. 10 is a front elevational view of one component of the latch mechanism shown in FIG. 8.
Figure 11:
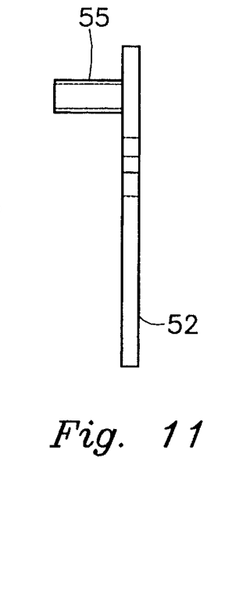
FIG. 11 is a side view of the component shown in FIG. 10.
Figure 12:
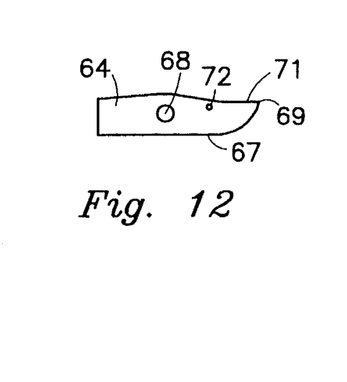
FIG. 12 is a front elevational view of the latch cover portion of the latch apparatus partially shown in FIG. 8.

Torsion spring 60 urges rotation of latch 52 in a counter-clockwise direction in the direction of arrow "C" shown in FIG. 8. Similarly, torsion spring 70 urges rotation of latch cover 64 in a clockwise direction shown by arrow "D" in FIG. 8.

Figure 13:
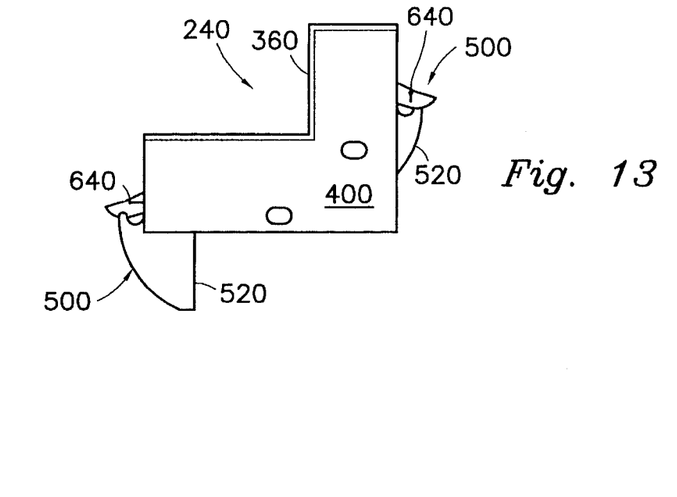
FIG. 13 is an another embodiment of the suspension apparatus shown in FIG. 7 taken from the same view.

FIG. 13 shows an alternate embodiment of a suspender 240. Base plate 360 is shaped in a "L" shape as are end plates 400. Suspender 240 includes two blocking mechanisms 500, each locking mechanism 500 including a latch 520 and a latch cover 640 in the same manner as suspender 24 from FIG. 7.

Figure 14:
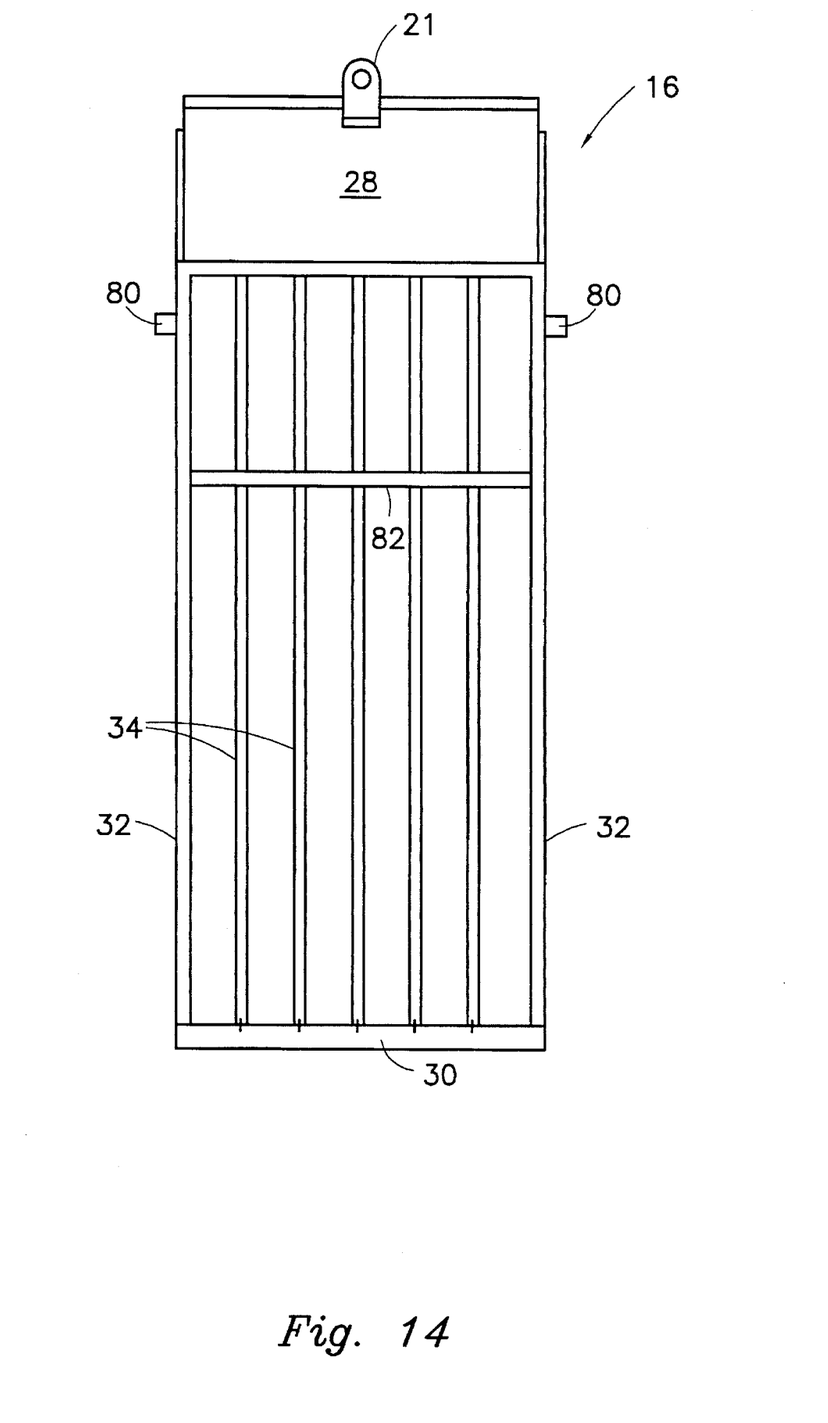
FIG. 14 is an enlarged schematic view of one side of a module that may be suspended with the suspension apparatus of the invention.

FIG. 14 shows a module 16 having essentially the same construction as the modules shown in FIGS. 1–3 including housing 28, lifting eyes 21, legs 32, lamps 34 and lower header 30. Module 16 further contains a pair of horizontally oriented lifting pegs 80 extending outwardly from opposing legs 32. Also, an "L" shaped lifting bar 82 is affixed between opposing legs 32 and located approximately one-third of the distance downwardly from the top of housing 28.

Details of the methodology for suspending a module 16 in accordance with the invention are described below in conjunction with FIGS. 4, 6 and 15–20.

Figure 4:
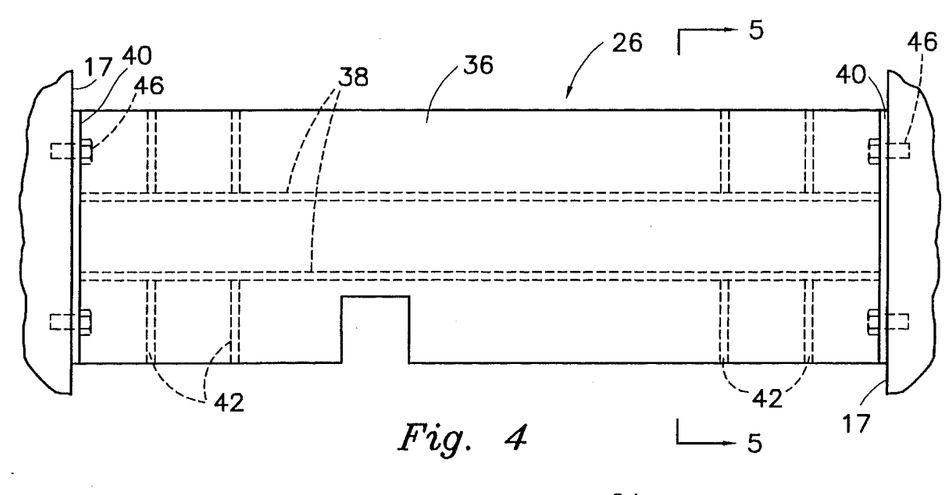
FIG. 4 is a top plan view of a portion of the suspension apparatus mounted between channel walls in accordance with the invention.
Figure 5:
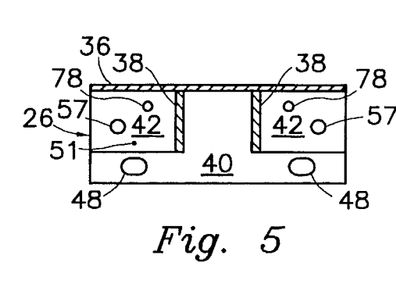
FIG. 5 is a cross sectional view taken along the lines and arrows 5—5 of FIG. 4.

As shown in FIGS. 4 and 6, suspenders 24 are fixed in a desired position both vertically and horizontally against channel walls 17 and 19 of FIG. 1. Preferably, a suspender 24 is located between all of the adjacent rows of modules 16. When one or more modules 16 are desired to be suspended, crane 18 swings outwardly over the targeted module and lifting eyes 21 are used to engage lifting rod 23, which connects to lifting wire 25. Wire 25 is retracted, thereby raising module 16 substantially vertically upwardly. Upward movement simultaneously causes lifting pegs 80 to move substantially vertically upwardly in a like manner. Reverse directional movement of wire 25 causes downward movement of module 16 and lifting pegs 80.

Figure 15:
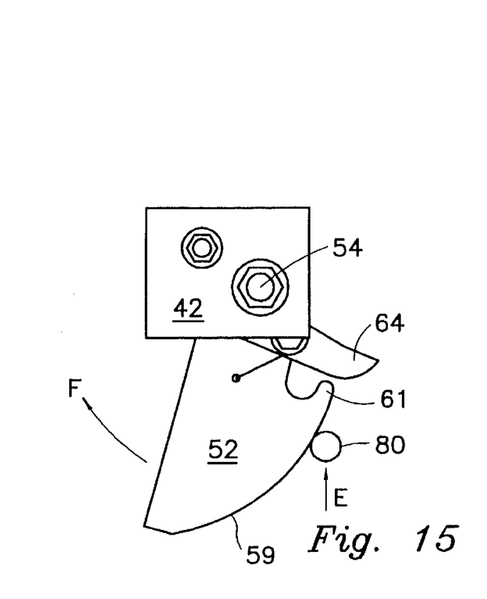
FIG. 15 is an enlarged view of the apparatus shown in FIG. 8 having components in a first rotational position.

For sake of simplicity, FIGS. 15–20 show relative vertical movement of lifting peg 80 through a full suspension cycle and then module removal. Lifting pegs 80 are shown as the lifting mechanism of the modules for the sake of convenience although other lifting constructions may be used as described elsewhere. For example, as shown in FIG. 15, peg 80 (and therefore module 16 which is not shown for simplicity) has moved upwardly in the direction shown by the arrow "E". Lifting peg 80 engages curved surface 59 of latch 52, causing latch 52 to rotate in a clockwise direction as shown by arrow "F" and away from the "normal" or "at rest" position of latch 52 shown in FIGS. 7 and 8. Latch cover 64 has not rotated substantially, despite the clockwise direction urging of torsion spring 70 because latch screw 54 acts as a "stop" member to maintain latch cover 64 substantially in a "closed" position.

Figure 16:
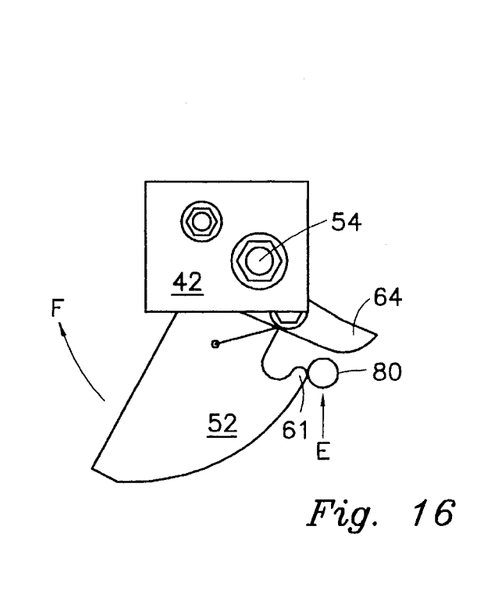
FIG. 16 is an enlarged view of the apparatus shown in FIG. 8 having components in a second rotational position.

Further upward vertical movement of lift peg 80 as shown in FIG. 16 causes latch 52 to rotate further in the direction of arrow "F" to a maximum rotation point when locking tip 61 engages lift peg 80. Latch screw 54 continues to prevent further substantial clockwise rotation of latch cover 64, thereby causing latch cover 64 to be positioned into an "open" position.

Figure 17:
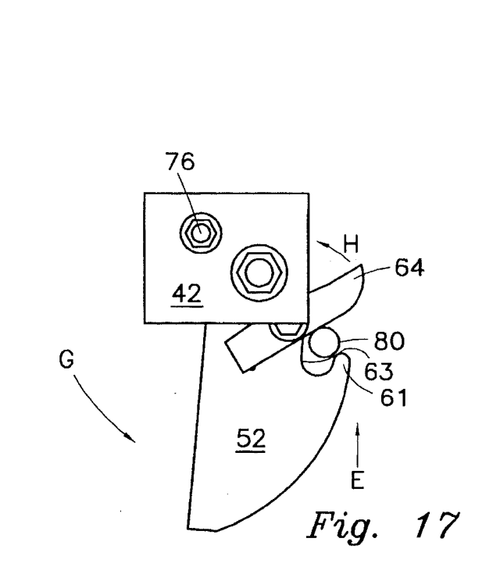
FIG. 17 is an enlarged view of the apparatus shown in FIG. 8 having components in a third rotational position.

FIG. 17 shows still further upward vertical movement of lifting peg 80 in direction "E" such that lifting peg 80 vertically clears locking tip 61. Clearance of locking tip 61 by lifting peg 80 permits rotation of latch 52 in a counterclockwise direction as shown by arrow "G". Rotation of latch 52 in direction "G" causes locking wall 63 to engage lifting peg 80, thereby partially terminating further counterclockwise rotation of latch 52 in direction "G". Stop screw 76 also prevents further counterclockwise rotation of latch 52.

Figure 18:
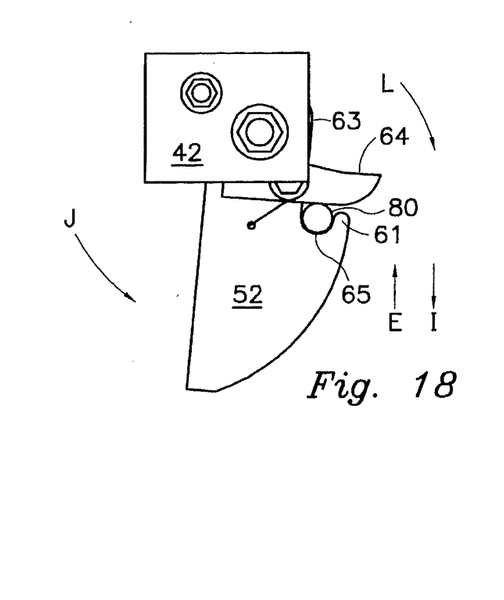
FIG. 18 is an enlarged view of the apparatus shown in FIG. 8 having components in a fourth rotational position.

Slight downward vertical movement of lifting peg 80 as shown in FIG. 18 by arrow "I" causes lifting peg 80 to move along locking wall 63 and into engagement with locking grove 65. At the same time, latch cover 64 rotates in a clockwise direction as shown by arrow "L" and engages the upper side of lifting peg 80. This results in the securing of lifting peg 80 and its associated module 16 into the desired suspended position.

Figure 19:
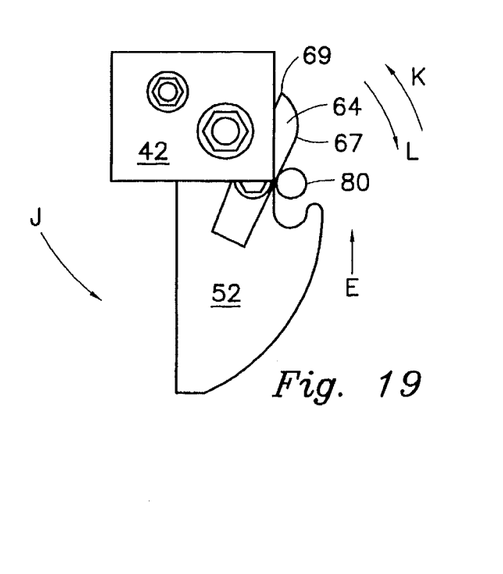
FIG. 19 is an enlarged view of the apparatus shown in FIG. 8 having components in a fifth rotational position.
Figure 20:
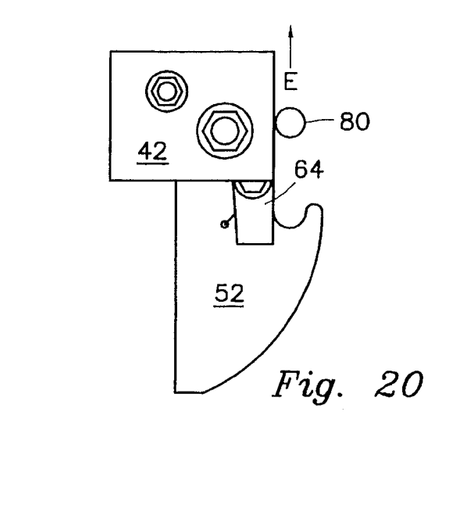
FIG. 20 is an enlarged view of the apparatus shown in FIG. 8 having components in a sixth rotational position.

When it is desired to remove module 16 from channel 12 when it is located in suspender 24, the action shown in FIGS. 19 and 20 occurs. However, in the case where module 16 is moved from the bottom of the channel, the action shown in FIGS. 15–17 occurs first. In other words, lifting peg 80 engages curved surface 59 of latch 52, thereby causing it to rotate clockwise in the direction of letter "F" as shown in FIG. 15. Further raising of the module and lifting peg 80 causes latch 52 to continue rotation in a clockwise direction in the direction of arrow "F" up to and past locking tip 61 as shown in FIG. 16. Further movement of module 16 and lifting peg 80 permits latch 52 to "spring" back into its "at rest" position by rotation in a counterclockwise direction as shown by letter "G" in FIG. 17. Next, further lifting results in engagement of lifting peg 80 with under surface 67 of latch cover 64, thereby rotating it counterclockwise in the direction shown by letter "K" in FIG. 19. Then, continued vertical upward movement of lifting peg 80 causes latch cover 64 to rotate into a substantially vertical position to thereby cause an open and clear pathway for lifting peg 80 to continue vertically beyond mounting plate 42 and upwardly beyond suspender 24 and out of the channel.

In the case where module 16 is removed from a suspender 24, the steps described above with respect to FIGS. 19–20 only occur. In that case, upward movement avoids downward movement as shown in FIG. 18. As shown in FIGS. 19 and 20, latch cover 64 rotates in the direction of arrow "K" until lifting peg 80 has cleared its outermost tip 69. At that point, latch cover 64 rapidly rotates or "springs" in a clockwise direction shown by arrow "L" into the "at rest" position shown in FIG. 8. Latch 52 remains in its rest position against stop screw 76 which prevents its further rotation in a direction shown by arrow "J".

Figure 21:
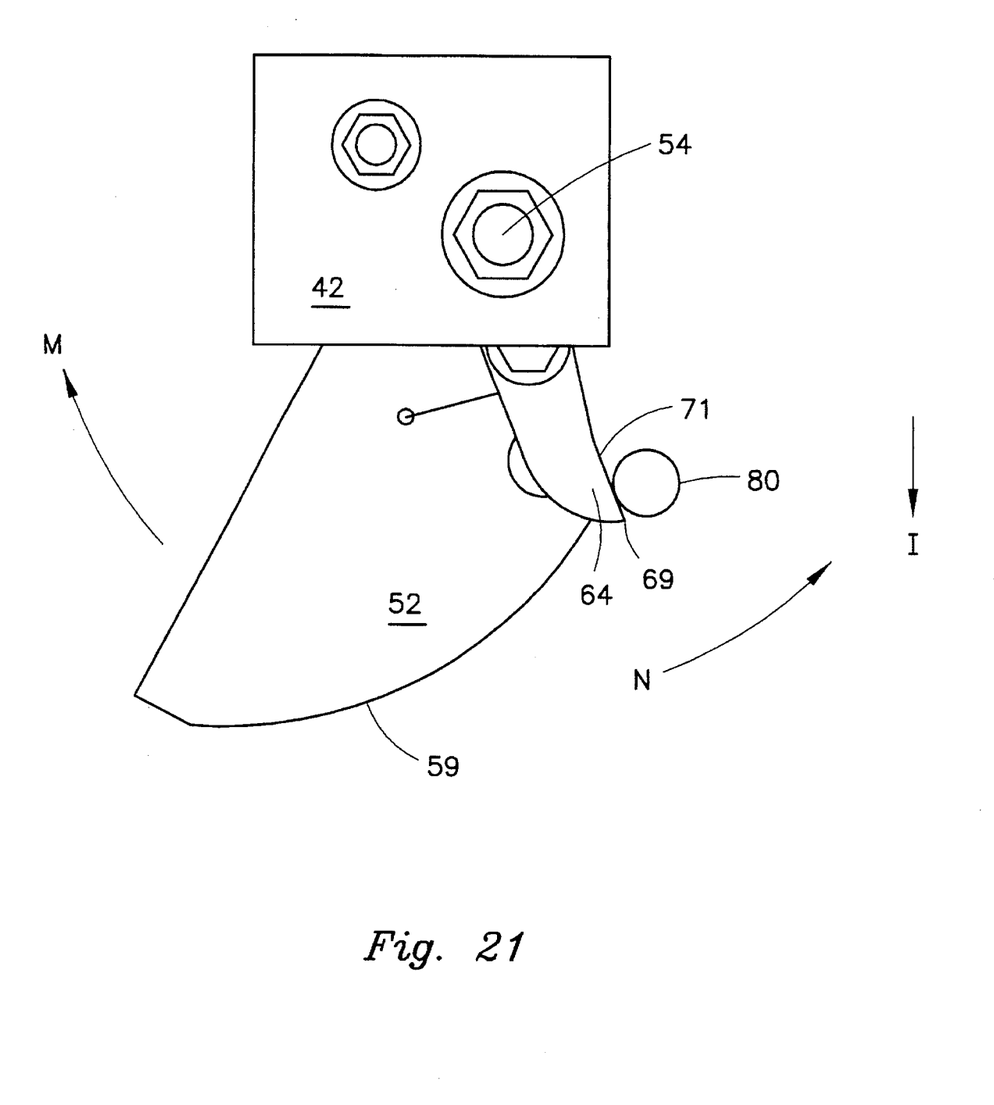
FIG. 21 is an enlarged view of the apparatus shown in FIG. 8 having components in a seventh rotational position.

Placement of a module 16 into a channel after complete removal or as an initial placement is easily achieved without interference from suspenders 24 as shown in FIG. 21. In such a case, lifting peg 80 engages top surface 71 of latch cover 64 as it moves in the direction shown by arrow "I", thereby causing it to force rotation of latch 52 in a clockwise direction as shown by arrow "M" until lifting peg 80 clears tip 69 of latch cover 64. Once lifting peg 80 has cleared tip 69, latch 52 rotates in a counterclockwise direction as shown by arrow "N" toward its rest position and into engagement with curved surface 59 (not shown). Further downward movement of lifting peg 80 permits further counterclockwise rotation of latch 52 along curved surface 59 into its rest position as shown in FIG. 8.

Through use of suspenders 24 in accordance with the invention, it is now possible to suspend modules at a desired vertical position above the floor of waste water channels to ease in periodic analysis, maintenance, monitoring and the like of modules 16. Also, modules 16 can be suspended individually or in groups to permit more efficient disinfection during low flow periods. Similarly, in flood conditions, modules 16 may be suspended in a manner that the electronic equipment enclosed in housing 28 remains high above maximum flood water levels to avoid damage.

Although this invention has been described with reference to specific forms selected for illustration in the drawings, it will be appreciated that many modifications may be made, that certain steps may be performed independently of other steps and that a wide variety of equivalent forms of apparatus may be used, all without departing from the spirit of this invention, which is defined in the appended claims. For example, a wide variety of materials, such as stainless steel, may be chosen for the module 16 and suspenders 24. Various changes in shape to the suspenders may be made such as the alternate embodiment depicted in FIG. 13, for example. It is also possible to employ suspenders having locking mechanisms 50 only on one side, if desired. Further, the number of locking mechanisms 50 is not limited for a particular suspender 24. For example, in the case where lifting bar 82, as shown in FIG. 14 is employed, multiple locking mechanisms 50, such as two, three, four or more, may be employed. Similarly, various shapes and sizes of lifting pegs 80 may be used as well as materials of construction. Lifting bar 82 may be made from a variety of different types and shapes of materials and may be located in any number of locations vertically along legs 32 of module 16. Similarly, an overlapping extending portion of the bottom of housing 28 may be employed as a lifting surface for engagement with latch 52. Moreover, although the invention has been described with respect to vertically oriented lamps 34, it is fully within the scope of the invention that modules employing horizontally oriented or other orientation of lamps 34 may be employed. Alternate module shapes may also be used in place of the shape of modules 16 shown and described herein so long as they have latch 52 engaging surfaces, pegs, brackets or the like. Also, suspenders 24 may be removably fixed to channel walls or fixed to other stable structures in the channel or out of the channel.

What is claimed is:

1. Apparatus for positioning a module containing at least one ultraviolet lamp relative to a passageway in which fluid to be treated flows comprising:
    a base member fixed to stable structure associated with said passageway;
    a suspender connected to said base member, said suspender including:
        a rotatably mounted latch having a module engaging portion sized and shaped to engage a module latch receiver associated with said module;
        biasing means associated with said latch and adapted to urge rotation of said module engaging portion toward and into engagement with said module latch receiver; and
        a rotatably mounted latch cover positioned adjacent said latch.

2. The apparatus defined in claim 1 further comprising biasing means associated with said latch cover to urge rotation of said latch cover in a direction opposite the direction of rotation urged by said latch biasing means.

3. The apparatus defined in claim 2 wherein said latch biasing means and said latch cover biasing means are springs.

4. The apparatus defined in claim 2 wherein said latch cover and said latch cover biasing means are mounted on a second pin.

5. The apparatus defined in claim 4 wherein said latch is mounted on a first pin connected between a pair of mounting plates connected to said base member, said first pin limiting the rotation of said latch cover.

6. The apparatus defined in claim 5 further comprising a third pin connected between said mounting plates and positioned to limit rotation of said latch.

7. The apparatus defined in claim 1 wherein said base member is elongated and has suspenders positioned at its end portions, each suspender engaging separate module latch receivers associated with said module.

8. The apparatus defined in claim 7 wherein said module latch receivers are pegs.

9. The apparatus defined in claim 7 wherein said module latch receivers are "L" shaped brackets.

10. The apparatus defined in claim 7 wherein each suspender engages a single module latch receiver associated with said module.

11. The apparatus defined in claim 10 wherein said receiver is an elongated member connected between legs of said module.

12. The apparatus defined in claim 1 wherein said base member is elongated and has at least four suspenders positioned at its end portions, the suspenders at each end portion facing in opposite directions to engage module latch receivers associated with separate but adjacent modules.

13. The apparatus defined in claim 1 wherein said latch and said latch biasing means are mounted on a first pin connected between a pair of mounting plates connected to said base member.

14. The apparatus defined in claim 1 wherein said base member is removably fixed to said stable structure.

15. The apparatus defined in claim 1 wherein said passageway is a channel with opposed walls comprising said stable structure and said base member is fixed between said walls.

16. Apparatus for positioning a module containing at least one ultraviolet lamp relative to a channel through which a stream of fluid to be disinfected flows comprising:
    a base member connected between opposed sides of said channel; and
    at least two suspenders connected to said base member, each suspender including:
        a suspension hook having a module engaging tip shaped and sized to engage a hook receiver associated with said module, said suspension hook being rotatably mounted on a first pin connected between a pair of plates fixed to said base member;
        a spring associated with said suspension hook adapted to urge rotation of said module engaging tip toward an adjacent module;
        a suspension hook cover mounted on a second pin associated with said suspension hook, said suspension hook cover being rotatable relative to said suspension hook; and
        a spring associated with said suspension hook cover adapted to urge rotation of said suspension hook cover in a direction opposite the rotation urged by said suspension hook spring.

17. The apparatus defined in claim 16 further comprising a stop member positioned adjacent said suspension hook to limit rotation of said suspension hook.

18. The apparatus defined in claim 16 wherein said base member is elongated and has two suspenders positioned at each end portion of said base member, each pair of suspenders at each end portion facing in opposing directions.

19. Apparatus defined in claim 16 wherein said base member is elongated and has two suspenders positioned at each end portion of said base member, each suspender engaging separate hook receivers associated with separate adjacent modules.

* * * * *